United States Patent
Burgo

(10) Patent No.: US 8,163,274 B2
(45) Date of Patent: Apr. 24, 2012

(54) PERSONAL CARE PRODUCTS CONTAINING HIGH REFRACTIVE INDEX ESTERS AND METHODS OF PREPARING THE SAME

(76) Inventor: Rocco Burgo, Mullica Hill, NJ (US)

( * ) Notice: Subject to any disclaimer, the term of this patent is extended or adjusted under 35 U.S.C. 154(b) by 853 days.

(21) Appl. No.: 11/895,759

(22) Filed: Aug. 27, 2007

(65) Prior Publication Data

US 2007/0292374 A1  Dec. 20, 2007

Related U.S. Application Data

(63) Continuation of application No. 10/819,589, filed on Apr. 7, 2004, now abandoned.

(51) Int. Cl.
*A61K 31/74* (2006.01)
(52) U.S. Cl. ........................ 424/78.03; 525/82
(58) Field of Classification Search ............... 424/78.03; 525/82
See application file for complete search history.

(56) References Cited

U.S. PATENT DOCUMENTS

| | | | |
|---|---|---|---|
| 4,606,916 A | 8/1986 | Hofinger et al. | |
| 4,853,430 A | 8/1989 | Stühler et al. | |
| 4,975,523 A | 12/1990 | Altounian | |
| 5,066,484 A | 11/1991 | Castrogiovanni et al. | |
| 5,145,671 A | 9/1992 | Castrogiovanni et al. | |
| 5,158,762 A | 10/1992 | Pierce | |
| 5,160,738 A | 11/1992 | Macaulay et al. | |
| 5,164,471 A | 11/1992 | O'Lenick, Jr. | |
| 5,210,133 A | 5/1993 | O'Lenick, Jr. | |
| 5,624,676 A | 4/1997 | Mackey et al. | |
| 5,840,292 A | 11/1998 | Lee et al. | |
| 6,013,271 A | 1/2000 | Doughty et al. | |
| 2003/0003069 A1* | 1/2003 | Carson et al. ................. | 424/70.1 |
| 2005/0008586 A1 | 1/2005 | Bertz et al. | |
| 2005/0152858 A1 | 7/2005 | Bertz et al. | |
| 2006/0067900 A1 | 3/2006 | Bertz et al. | |
| 2006/0067901 A1 | 3/2006 | Bertz et al. | |

FOREIGN PATENT DOCUMENTS

| EP | 0229400 | 7/1987 |
|---|---|---|
| EP | 0551749 A2 | 7/1993 |
| GB | 2064567 A | 6/1981 |
| GB | 2119393 A | 11/1983 |
| JP | 51-87479 A2 | 7/1976 |
| WO | WO 96/06878 A1 | 3/1996 |

OTHER PUBLICATIONS

Opgrande et al., "Bezoic Acid", May 16, 2003, Kirk-Othmer Encyclopedia of Chemical Technology, pp. 625-637.*
Chemspider Beta, "Inherent Properties, Identifiers and References", Jan. 3, 2008.*
http://www.yeeyong.co.kr, "Dipropylene Glycol Dibenzoate", May 2002.*

* cited by examiner

*Primary Examiner* — Karlheinz R Skowronek
*Assistant Examiner* — Ali Soroush
(74) *Attorney, Agent, or Firm* — Flaster/Greenberg PC

(57) ABSTRACT

The invention includes personal care compositions and methods of preparing these personal care compositions that include incorporation of a polyol polyester that is the reaction product of an aliphatic polyol that does not contain an ether group, and benzoic acid, wherein the resultant polyol polyester has a refractive index at 25° C. of greater than about 1.5. The aliphatic polyol may have two to three carbon atoms. Alternatively, the invention includes personal care compositions and methods of preparing personal care compositions including incorporating a polyol polyester into a personal care formulation. The polyol polyester is represented by formula (I):

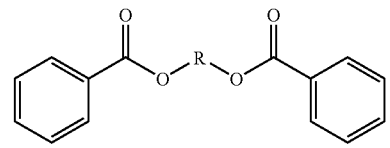

wherein R is an aliphatic alkyl group that does not contain an ether group and has a refractive index of greater than about 1.5 at 25° C. Also described are methods of preparing personal care compositions comprising a first phase and a second phase, wherein the second phase contains any of the polyol polyesters described above.

10 Claims, No Drawings

PERSONAL CARE PRODUCTS CONTAINING HIGH REFRACTIVE INDEX ESTERS AND METHODS OF PREPARING THE SAME

CROSS-REFERENCE TO RELATED APPLICATIONS

This application is a Continuation application of co-pending U.S. patent application Ser. No. 10/819,589 filed Apr. 7, 2004, the disclosure of which is incorporated by reference in its entirety.

BACKGROUND OF THE INVENTION

Conventional personal care products including cosmetic compositions that are topically applied to the skin and hair often contain ester oils. Incorporation of ester oils into these products provides benefits such as improvement of the softness and smoothness of the skin and conditioning effects to the hair (for example, by reducing the force required to comb wet or dry hair). When incorporated into personal care products, ester oils tend to contribute substantiveness, e.g, they adhere to the substrate (hair shaft or stratum corneum) due to their polarity and they additionally provide the aforementioned benefits without contributing negative aesthetics such as oiliness and greasiness.

Shine, gloss, and clarity are attributes that are often highly desired in personal care products, especially those that are applied to the skin, hair and nails. For example, shine and gloss are especially important in products such as lipsticks, lip glosses (clear or pigmented), and other cosmetics used to impart color to the skin ("decorative cosmetics"). Clarity is a particularly desirable characteristic in an antiperspirant composition. For hair care products, shine and gloss are highly desired, mostly in applications such as hair tonics, mousses, setting lotions, dressings, and conditioning compositions.

Personal care products, such as the cosmetic compositions described above, are typically applied as a composition that has the form of an emulsion, a solution, a suspension, a gel, and/or a solid. After application, a layer consisting of a mixture of the non-volatile, non-penetrating ingredients is left on the surface of the substrate. It is this layer that provides the desired color, aesthetic, beautification, and/or therapeutic benefit.

The attributes of shine and gloss are directly related to the smoothness of the surface layer after application and to the aggregate reflectivity of the components that comprise the layer. The Fresnel law of diffraction states that the intensity of a reflected beam of light emanating from air that is incident on a surface of a material is a function of: (1) the angle of incidence, (2) the polarization of the incident beam, and (3) the index of refraction of the material. Reflectivity ("R") is defined as the ratio of the intensity of the reflected beam ("$I_r$") to the intensity of the incident beam ("$I_i$"). By application of the Fresnel law, the equation relating R to the refractive index of the surface material ("n") is given by:

$$R = I_r/I_i = (n-1)^2/(n+1)^2$$

Thus, the higher the refractive index of the layer of personal care product, the greater its reflectivity.

In the case of a personal care product, the material that comprises the surface layer is a mixture of non-volatile, non-penetrating ingredients that may not be miscible in one another. Various equations have been developed using a combination of the electromagnetic theory of light and empirical methods to predict the refractive index of mixtures. The most widely used mixing rule for the prediction of the refractive index of binary systems is that of Lorentz-Lorenz. The Lorentz-Lorenz equation states that the square of the mixture refractive index minus one divided by the square of the mixture refractive index plus two is equivalent to the sum of the volume fraction of the individual components, times their respective refractive index squared minus one divided by their square plus two respectively. This relation can be extended to include ternary, quaternary, and higher order mixtures.

In formulating a personal care product one may estimate the compositions of the immiscible phases in the surface layer to calculate their respective refractive indices. With this information, one may implement a formulation strategy to achieve clarity in the final formulation by matching the refractive indices of all phases within the surface layer. The lesser the difference between/among each of the refractive indices, the greater the clarity, shine and/or gloss of the final product.

In personal care products where clarity, shine and or/gloss may be desirable, the relatively low refractive indices of most ester oils makes it difficult to achieve these properties, as the formulations also contain primarily compounds of lower refractive indices, such as castor oil, high viscosity silicones (e.g., 100 centipoise to 1000 centipoise), film formers, and/or high viscosity esters. Yet, elimination of these compounds is undesirable as well, because of the advantageous properties they contribute to the formulation.

Thus, there is a need for liquid, light viscosity, non-irritating, non-penetrating esters for use in personal care compositions with high refractive indices, such that improved shine, gloss and clarity can be obtained. Moreover, personal care compositions with these esters incorporated into their formulations are also desirable.

SUMMARY OF THE INVENTION

The invention provides personal care compositions containing, liquid, light viscosity, non-irritating, non-penetrating polyol polyesters esters having high refractive indices, preferably greater than about 1.5 at 25° C. These personal care compositions, depending on their underlying formulation, exhibit improved shine, gloss, and/or clarity in comparison to prior art formulations.

The invention provides a method of preparing a personal care composition that includes reacting an aliphatic polyol having two to three carbon atoms, but which does not contain an ether group, and benzoic acid. The resultant polyol polyester has a refractive index at 25° C. of greater than about 1.5. The polyol polyester is incorporated into a personal care formulation and/or can be used to adjust the refractive index of a phase of a personal care composition having at least two phases.

The invention also includes methods of preparing personal care compositions that include incorporation of a polyol polyester into a personal care formulation. The polyol polyester is represented by the formula (I):

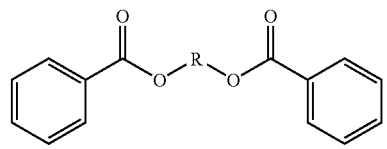

wherein R is an aliphatic alkyl group that does not contain an ether group. The polyol polyester has a refractive index of greater than about 1.5 at 25° C.

Also included is a personal care composition that contains a polyol polyester represented by formula (I):

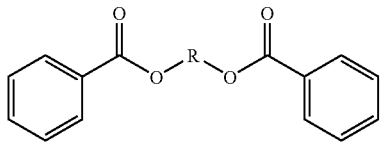

wherein R is an aliphatic alkyl group that does not contain an ether group. This polyol polyester may have a refractive index of greater than 1.5 at 25° C.

Methods of preparing two phase personal care compositions are also disclosed. The methods include mixing a first phase with a second phase, wherein the second phase includes a polyol polyester represented by the formula (I), above, and R is an aliphatic alkyl group that does not contain an ether group. In such methods, the refractive index of the first phase is substantially identical to the refractive index of the second phase.

Methods of preparing personal care compositions having refractive indices of greater than about 1.4 at 25° C. are also included. These methods include mixing at least one aliphatic ester with a polyol polyester that is represented by the formula (I) wherein R is an aliphatic alkyl group that does not contain an ether group and the composition has a refractive index of greater than about 1.4.

DETAILED DESCRIPTION OF THE INVENTION

The invention described herein relates to personal care products containing specific polyol polyesters to enhance the shine, gloss, and clarity exhibited by such compositions when applied to skin, hair, or nail surfaces. The invention provides non-penetrating, non-volatile, light viscosity, high refractive index ester oils in personal care compositions thereby providing benefits in skin, hair, and nail care applications such as improvements of shine, gloss, clarity, and other aesthetic and/or comfort-related properties of the composition. The specific polyol polyesters are incorporated into personal care formulations to prepare the personal care compositions of the invention.

By "personal care composition" it is meant any composition that is used or marketed as a material to be applied to skin, hair or nails and/or the stratum corneum of human or animal subjects for cosmetic, aesthetic and/or therapeutic effects, regardless of the delivery form of the composition and may include phases or intermediate preparations ultimately formulated into personal care products. Such compositions can include grooming products, such as soaps, cleansers, shampoos, skin or hair conditioners, shaving cream, lotions, and gels; hair sprays, gels, tonics, mousses, pomades, and lacquers; antiperspirants and deodorants; skin lotion, cream, mousse, and ointments, and nail and cuticle care products such as polishes and creams, and color-imparting cosmetics such as lipsticks, mascaras, foundations, eye shadows, and other decorative cosmetics.

The polyol polyester that is incorporated into the personal care product of the invention has a refractive index measured at 25° C. of greater than about 1.5 at 25° C., with a refractive index of about 1.5 to about 1.7 at 25° C. being preferred. Methods for empirically determining the refractive index of a given compound are well known in the art; any of these methods may be used. Preferred is the method using an Abbe refractomer, as described in, e.g., ASTM 1045-95 (2001), the contents of which are incorporated herein by reference.

The polyol polyester that is incorporated into the personal care product may be the reaction product of (a) an aliphatic polyol having two to three carbon atoms but that does not contain an ether group and (b) benzoic acid. Suitable aliphatic polyol(s) include all those known or to be developed in the art, so long as the alkyl group contains at least one, at least two, or at least three carbon atoms. A preferred aliphatic polyol has two to three carbon atoms. In addition, it is desirable that the selected aliphatic alkyl group does not contain an ether group along the backbone; the selected aliphatic alkyl group may be substituted or unsubstituted.

Exemplary aliphatic polyol(s) that may be reacted with benzoic acid include 1,2-ethanediol, 1,2-propanediol, or 1,3-propanediol. The resultant polyol polyester may be substituted at any location along the backbone with any functional, organic, or other group known in the art.

An exemplary polyol polyester is represented by the formula (I):

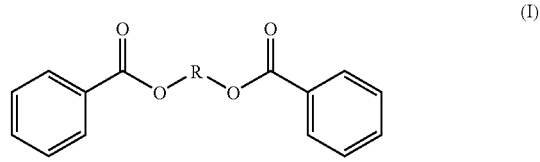

wherein R represents a substituted or unsubstituted aliphatic alkyl group. Any aliphatic alkyl group is suitable. However, aliphatic alkyl groups having at least one, at least two, or at least three carbon atoms in the backbone are preferred. Most preferred are those having two to three carbon atoms in the backbone. Additionally, it is preferred that the selected alkyl group does not contain an ether group within its backbone. The polyol polyester represented by formula (I) may be substituted at any location along the backbone with any functional, organic or other group known in the art.

The polyol polyester that is present in the personal care product of the invention preferably has a low, or light viscosity, as such low viscosity may make it more suitable for use in some personal care formulations. For example, the viscosity of the polyol polyester of the invention will range from about 30 cSt to about 200 cSt, more preferably 40 cSt to 100 cSt, and most preferably, 50 cSt to 80 cSt, each measured at 25° C. As will be understood by a person of skill in the art, the desired viscosity will depend on the personal care formulation into which the particular polyol polyester is to be incorporated.

Preferred polyol polyesters for use in the methods of the invention include ethylene glycol dibenzoate, propylene glycol dibenzoate, and 1,3-propanediol dibenzoate.

The invention also includes a method of preparing a personal care composition by incorporating the polyol polyester as described above into a personal care formulation. Any personal care formulation known or to be developed in the prior art is suitable for use in the method. The personal care formulation may be a formulation for any type of personal care product.

Exemplary formulations include those for soaps (liquid, solid, foam or mousse), cleansers, creams, lotions, ointments, suspensions, shampoos, deodorants, antiperspirants, conditioning products for hair, skin and nails and decorative cosmetics. The personal care formulations selected may include organic components, inorganic components; color active ingredients (e.g., pigments and dyes); therapeutic active ingredients (e.g., vitamins, alpha hydroxyacids, corticosteroids, amino acids, collagen, retinoids, anti-microbial compounds), sunscreens and/or UV absorbing compounds, reflective compounds, oils such as castor oil, olive oil; film formers, high viscosity oils, high molecular weight esters, high viscosity silicones, antiperspirant active ingredients, glycol solutions, water, alcohols, emulsifiers, gellants, volatile silicones, non-volatile silicones, emollients, water, polymers, hydrocarbons, and/or aliphatic esters.

Exemplary high molecular weight esters include pentaerythritol tetraisostearate (such as CRODAMOL® PTIS, Croda Corporation, Parsippany, N.J., U.S.A.) and dipentaerythritol hexa $C_5$-$C_9$ acid esters (such as LEXFEEL® 350, Inolex Chemical Company, Philadelphia, Pa., U.S.A.). In some cases such as in a formulation for a personal care product that is a decorative cosmetic, it may be desirable to disperse the color active ingredients (e.g., opaque or translucent pigments or dyes) in such high molecular weight esters and/or high viscosity oil, such as castor oil.

Exemplary high viscosity silicones that can be include in the personal care formulation include a two hundred (200) centistoke polydimethylsiloxane polymer (for example, 200 cSt Dow Corning 200 Fluid, Dow Corning Corporation, Midland, Mich., U.S.A.). Inclusion of these compounds may be suitable if one wishes to modify the smoothness and slip properties of the personal care product.

Typical film formers that can be used in the personal care formulation component of the invention include acrylate copolymers (such as AVALURE® AC120, Noveon Corporation, Cleveland, Ohio, U.S.A.), tricontanyl PVP (such as GANEX® WP-660, ISP Corporation, Wayne, N.J., U.S.A.), alpha-olefin/isopropyl maleate copolymer (such as PROFORMA® V1608, New Phase Technologies, Sugar Land, Tex., U.S.A.). In general, film formers will be included in the formulation when preparing a product intended to smooth out surface irregularities in the stratum corneum and to provide a stable, immovable matrix for any color active ingredients to be included.

The personal care formulation may be an antiperspirant including inorganic salts and/or inorganic salt/glycine complexes. Examples of antiperspirant active ingredients include, but are not limited to, activated aluminum chlorohydrate ("AACH"), aluminum zirconium polychlorhydrex-glycine complex ("ZAG") or activated ZAG ("AZAG"). The antiperspirant active ingredient may be provided to the formulation in any form, including a powder, an aqueous solution, or a glycol solution (e.g., propylene glycol, 1,3-butylene glycol, and dipropylene glycol).

These active ingredients and the solutions in which they are delivered have refractive indices typically exceeding 1.43. For example, a thirty percent (30%), non-aqueous solution of aluminum zirconium pentachlorohydrex-glycine complex in propylene glycol (such as, for example, WESTCHLOR® A2Z 8106 30% P.G. Solution, Westwood Chemical Corporation, Middletown, N.Y., U.S.A.) has a refractive index of 1.460 at 25° C. Propylene glycol, a commodity chemical, is commonly used as a non-volatile carrier for the active ingredient phase to lower the refractive index of that phase.

Conventional antiperspirant gels are microemulsions made up of two immiscible phases in which the particle size of the internal phase is typically less than one hundred (100) nanometers. In conventional practice, the formulation of clear antiperspirant gels will usually include the combination of an active ingredient phase and a vehicle phase. The active ingredient phase will normally include one or more of the aforementioned antiperspirant active ingredients, either dissolved or pre-dissolved in water, propylene glycol, other glycols, or mixtures thereof. The vehicle phase will typically include an emulsifier/gellant and a mixture of oily ingredients that are meant to ease the spreading of the antiperspirant product onto the skin, and to reduce the feeling of drag, greasiness and/or tackiness and/or to reduce the whitening effect often observed after antiperspirant products are applied and dry out. The most common emulsifier/gellants used in the formulation of clear antiperspirant gels are dimethicone crosspolymer and PEG-12 dimethicone crosspolymer, ordinarily supplied as a blend in cyclopentasiloxane (DOW CORNING® 9040 Silicone Elastomer Blend; DOW CORNING® 9011 Silicone Elastomer Blend, each available from Dow Corning Corporation, Midland, Mich., U.S.A.). Common oily ingredients that are used in the vehicle phase are volatile silicones, non-volatile silicones, hydrocarbons, and aliphatic esters. In order to obtain a clear or substantially transparent gel, it is important that the refractive index of the active ingredients phase and the vehicle phase match as closely as possible. Exemplary ingredients that may be included in the vehicle phase include dimethicones (DOW CORNING® 200 series Fluids, Dow Corning Corporation, Midland, Mich., U.S.A.) and cyclomethicones (DOW CORNING® 244, 245, 344, 345 Fluids, Dow Corning Corporation, Midland, Mich., USA).

The invention also includes a method of increasing the refractive index of a composition that includes incorporating into the composition an amount of the polyol polyester that is the reaction product of an aliphatic polyol and benzoic acid. The aliphatic polyol may be the same described above.

Also included in the invention is a method of preparing a composition that comprises mixing a first phase with a second phase, wherein the second phase includes a polyol polyester represented by the formula I:

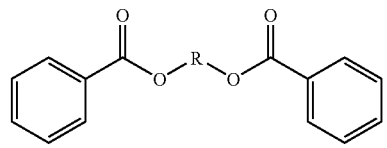

and R is an aliphatic alkyl group, as described above.

Further, the invention includes a method of preparing a composition having a refractive index of at least about 1.4 at 25° Celsius. This method includes mixing at least one aliphatic ester with a polyol polyester represented by formula (I), above, wherein the R is an aliphatic alkyl group that does not contain an ether group, and the composition has a refractive index of at least 1.4 at 25°.

Also included are methods of adjusting the refractive index of a phase of a personal care composition that comprises at least two phases and/or methods of preparing a personal care composition of at least two phases, wherein the refractive indices of the at least two phases are substantially identical. These methods include:

(i) preparing a first phase that has a refractive index of less than or equal to about 1.5,
(ii) preparing a second phase that has a refractive index that is lower than the refractive index of the first phase,
(iii) adding to the second phase an amount of a polyol polyester sufficient to reduce the difference between the refractive index of the first phase and that of the second phase, and
(iv) mixing the first phase with the second phase to prepare a personal care composition.

The polyol polyester is any one of those described above. It is preferred that the difference between the refractive indices of each of the phases after step (iii) is about 0.1 to about 0.5, more preferred that it is about 0.2 to about 0.5, and most preferred that it is less than about 0.5. Preferably, the difference is about zero.

In any of the methods of preparing a personal care composition disclosed herein, one may optionally mix the polyol polyester with an aliphatic ester to alter the "skin feel" of the polyol polyester. Any aliphatic ester is suitable, although preferred are isopropyl laurate, isopropyl myristate, isopropyl palmitate, ethylhexyl palmitate, neopentyl glycol diheptanoate, and/or trimethylolpropane tricaprylate/tricaprate.

The following examples provide illustrations of the methods and composition of the invention, but are in no way intended to be limiting. In each of the examples, color was evaluated using American Society of Testing Materials (ASTM) method D-1209 (1997). Acid value was measured using ASTM method D-974-95 (1995). Kinematic viscosity was measured using ASTM method D-445-97 (1997). Refractive index was measured using an Abbe digital refractometer. Odor was detected using subjective olfactory assessments.

The names for the components given in the personal care composition example are those used by the Cosmetic, Toiletry, and Fragrance Associates (CTFA), as set forth in the CTFA International Cosmetic Ingredient Dictionary and Handbook, $9^{th}$ ed. (2002).

EXAMPLE 1

Propylene glycol and benzoic acid were charged to a stirred batch reactor in a molar ratio of 1.02:2.00 and heated with inert gas sparging to 120 to 225° C. in the presence of a small quantity of a sulfonic acid catalyst. The acid value was monitored, and the reaction was stopped before the acid value reached 0.5. Remaining trace acid was neutralized with 15% sodium carbonate solution. The neutralized ester was then deodorized by steam stripping, and further purified with activated carbon, and then filtered. Table 1 shows the properties obtained.

TABLE 1

Properties of propylene glycol dibenzoate ester.

| Property | Result |
|---|---|
| Color, APHA | 10 |
| Acid Value, mg KOH/g | 0.01 |
| Kinematic Viscosity @ 25° C., cSt | 70 |
| Odor | Faint |
| Refractive Index @ 25° C. | 1.545 |

This propylene glycol dibenzoate ester was incorporated into a personal care formulation to prepare a personal care composition.

EXAMPLE 2

Ethylene glycol and benzoic acid were charged to a stirred batch reactor in a molar ratio of 1.02:2.00 and heated with inert gas sparging to 120 to 225° C. in the presence of a small quantity of catalyst, sulfonic acid catalyst. The acid value was monitored, and the reaction was stopped before the acid value reached 0.5. Remaining trace acid was neutralized with a 15% sodium carbonate solution. The neutralized ester was then deodorized by steam stripping, and further purified with activated carbon, and then filtered. Table 2 shows the properties obtained.

TABLE 2

Properties of ethylene glycol dibenzoate ester.

| Property | Result |
|---|---|
| Color, APHA | 5 |
| Acid Value, mg KOH/g | 0.01 |
| Kinematic Viscosity @ 25° C., cSt | 54 |
| Odor | Faint |
| Refractive Index @ 25° C. | 1.552 |

EXAMPLE 3

The following composition illustrates the preparation of a personal care composition of the invention that is a styling spray for the hair that provides a high degree of shine in addition to the ordinary benefits achieved through use of a hair spray or styling spray. A styling spray formulation was devised and a polyol polyester in accordance with the invention was incorporated, as follows. The personal care composition styling spray contain the following ingredients:

| Formulation Ingredients | Parts By Weight % |
|---|---|
| SD Alcohol 40-B | 80.00 |
| Neopentyl glycol diheptanoate (and) isododecane | 5.00 |
| VP/VA Copolymer (and) Water | 5.00 |

The ingredients were combined in a vessel with gentle agitation with propylene glycol dibenzoate (10.00 wt %) until a clear, uniform solution is obtained. The mixture was then poured into a suitable container. The resultant styling spray imparted a shine to the hair when applied.

EXAMPLE 4

The following composition illustrates the preparation of a personal care composition of the invention that is a hair relaxer emulsion that leaves the hair shiny in addition to the ordinary benefits achieved through use of a hair relaxer. A hair relaxer formulation was devised and a polyol polyester in accordance with the invention was incorporated as follows.

| A formulation was prepared (all parts given in grams): | |
|---|---|
| Part A | |
| Deionized Water | 87.55 |
| Carbomer | 0.70 |
| Propylene Glycol | 1.00 |
| Methylparaben | 0.20 |
| Propylparaben | 0.05 |
| Part B: | |
| Neopentyl glycol diheptanoate (and) isododecane | 3.50 |
| Polysorbate 80 | 1.50 |
| Part C: | |
| Triethanolamine | 1.00 |
| Part D | |
| VP/VA Copolymer (and) Water | 1.00 |

The ingredients of Part A were combined in a vessel and warmed to about 70 to about 75° C. with vigorous agitation until a clear, uniform solution is obtained. The ingredients of Part B and 3.5 grams of propylene glycol dibenzoate were combined in a separate vessel and warmed to about 70 to about 75° C. until a clear solution is obtained. The solution of Part B was added to that of Part A by mixing under high shear. Mixing and heating are stopped, and Part C, triethanolamine is added. The solution is allowed to cool to about 40 to about 45° C. Part D is added. The solution is allowed to cool to room temperature with gentle agitation. The resulting emulsion is poured into canisters. Use of the composition results in relaxed hair with shine.

EXAMPLE 5

The following composition illustrates the preparation of a personal care composition of the invention that is a lipstick of high gloss. A lipstick formulation was devised, and a polyol polyester in accordance with the invention was incorporated as follows.

| Ingredients (given in grams) | |
| --- | --- |
| *Euphorbia cerifera* (candelilla) wax | 11.00 |
| Ozokerite | 3.00 |
| Microcrystalline wax | 3.00 |
| Ethylhexyl palmitate | 10.00 |
| *Ricinus communis* (castor) seed oil | 40.40 |
| Tocopheryl acetate | 0.50 |
| Propylparaben | 0.10 |

The *euphorbia cerifera* (candelilla) wax, ozokerite, microcrystalline wax, ethylhexyl palmitate, *Ricinus communis* (castor) seed oil, tocopheryl acetate, and propylparaben, were combined with 20.00 grams of propylene glycol dibenzoate in a vessel and warmed to about 80 to about 85° C. with gentle agitation until a clear, uniform solution is obtained. Mica (and) titanium dioxide (4 grams) and mica (and) iron oxides (8 grams) were individually added to this mixture under moderate agitation until a uniform solution is obtained. The heating was stopped and the solution was permitted to cool to about 65 to about 70° C. under gentle agitation. The resulting mixture was poured into a lipstick mold heated to 45° C. and allowed to cool to room temperature.

EXAMPLE 6

The following composition illustrates the preparation of a personal care composition of the invention that is a hair styling wax that provides a high degree of shine in addition to the ordinary benefits achieved through use of a hair wax. A hair styling wax formulation was devised and a polyol polyester in accordance with the invention was incorporated, as follows.

| Ingredients (amounts given in weight percent) | |
| --- | --- |
| Neopentyl glycol diheptanoate (and) isododecane | 73.50 |
| Ozokerite | 11.00 |
| Laureth-7 | 5.50 |

The neopentyl glycol diheptanoate (and) isododecane, laureth-7, and ozokerite were combined with propylene glycol dibenzoate (10.00 wt %) in a vessel and warmed to about 80 to about 85° C. with gentle agitation until a clear, uniform solution was obtained. The heating was stopped and the solution was allowed to cool to about 60 to about 65° C. under gentle agitation. The mixture was then poured into a suitable container and allowed to cool to room temperature.

EXAMPLE 7

The following composition illustrates the preparation of a personal care composition of the invention that is an antiperspirant stick that leaves a minimal white residue when applied, in addition to the ordinary benefits achieved through use of an antiperspirant stick. An antiperspirant stick formulation was devised and a polyol polyester in accordance with the invention was incorporated, as follows.

| Ingredients (amounts are given in weight percent) | |
| --- | --- |
| Hydroxystearic acid | 10.00 |
| Neopentyl glycol diheptanoate (and) isododecane | 46.00 |
| Propylene glycol dibenzoate | 10.00 |
| Talc | 6.00 |
| Aluminum zirconium tetrachlorohydrex/glycine | 24.00 |
| Amorphous fumed silica | 4.00 |

Hydroxystearic acid, neopentyl glycol diheptanoate (and) isododecane, in the amounts given above, were combined with propylene glycol dibenzoate (10.00) in a vessel and warmed to about 80° to about 85° C. with gentle agitation until a clear solution is obtained. Subsequently, the mixture was allowed to cool to about 70° C. The talc, aluminum zirconium tetrachlorohydrex/glycine and amorphous fumed silica were then added to the mixture. The mixture was agitated until uniform, then cooled to about 70° C. to about 72° C. The resulting mixture was poured into canisters at about 70° to about 72° C. and allowed to cool to room temperature.

EXAMPLE 8

This formulation illustrates the use of the invention that results in a clear antiperspirant gel that contains no water.

| Ingredients (amounts given in grams) | |
| --- | --- |
| Cetyl polyethylene glycol/polypropylene glycol-10/1 dimethicone | 3.00 |
| Neopentyl glycol diheptanoate (and) isododecane | 11.50 |
| Aluminum zirconium tetrachlorohydrex/glycine/propylene glycol (30% active ingredient) | 80.00 |

In a vessel equipped with propeller agitation, cetyl polyethylene glycol/polypropylene glycol-10/1 dimethicone and neopentyl glycol diheptanoate (and) isododecane were combined at a temperature of about 20° C. to about 25° C. The aluminum zirconium tetrachlorohydrex/glycine/propylene glycol (30% active ingredient) was then added slowly and carefully over a period of from about 15 to about 25 minutes. With vigorous propeller agitation, propylene glycol dibenzoate (5.50 grams) was then added until the emulsion exhibits the desired degree of clarity. The emulsion was then poured off to suitable containers.

What is claimed is:

1. A method of preparing a highly refractive personal care composition, the method comprising:
    (a) reacting an aliphatic polyol having two to three carbons atoms, which does not contain an ether group, and benzoic acid, to obtain a polyol polyester having a refractive index at 25° C. of greater than about 1.5; and
    (b) incorporating the polyol polyester into a personal care composition, wherein the personal care composition is selected from the group consisting of a soap, a cleanser, a shampoo, a skin conditioner, a hair conditioner, a hair spray, a hair gel, a hair tonic, a hair mousse, a hair pomade, a hair lacquer, a skin lotion, a skin cream, a skin mousse, a skin ointment, a lipstick, a mascara, a foundation, an eye shadow, or a color-imparting cosmetic, wherein the personal care composition has shine and gloss properties based on the refractive index of the polyol polyester, wherein the polyol polyester has a viscosity of about 30 to about 200 centistokes at 25° C.

2. The method of claim 1, wherein the polyol polyester has a viscosity of about 50 to about 70 centistokes.

3. The method of claim 1, wherein the aliphatic polyol is selected from the group consisting of propylene glycol, ethylene glycol, and 1,3-propanediol.

4. The method of claim 1, wherein the refractive index of the polyol polyester is about 1.54 to about 1.60 at 25° C.

5. The method of claim 1, wherein the personal care composition further comprises one or more of a material selected from the group consisting of water, a pigment, an emollient, a therapeutic active ingredient, an aliphatic ester, an emulsifier, and a polymer.

6. A method of preparing a highly refractive personal care composition comprising incorporating a polyol polyester into the personal care composition, wherein the polyol polyester is represented by the formula (I):

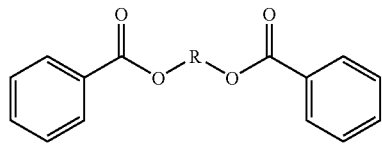

(I)

wherein R is an aliphatic alkyl group that does not contain an ether group and has a refractive index of greater than about 1.5 at 25° C. and wherein the personal care composition is selected from the group consisting of a soap, a cleanser, a shampoo, a skin conditioner, a hair conditioner, a hair spray, a hair gel, a hair tonic, a hair mousse, a hair pomade, a hair lacquer, a skin lotion, a skin cream, a skin mousse, a skin ointment, a lipstick, a mascara, a foundation, an eye shadow, or a color-imparting cosmetic, wherein the personal care composition has shine and gloss properties based on the refractive index of the polyol polyester, wherein the polyol polyester has a viscosity of about 30 to about 70 centistokes at 25° C.

7. The method of claim 6, wherein the personal care composition further comprises at least one of water, a pigment, an emollient, a therapeutic active ingredient, an aliphatic ester, an emulsifier, and a polymer.

8. The method of claim 6, wherein the polyol polyester has a viscosity of about 50 to about 70 centistokes.

9. The method of claim 6, wherein the refractive index of the polyol polyester is about 1.54 to about 1.60 at 25° C.

10. The method of claim 6, wherein the step of incorporating further includes the step of adding the polyol polyester in an amount sufficient to adjust the refractive index of the personal care composition to about 1.4 at 25° C.

* * * * *

UNITED STATES PATENT AND TRADEMARK OFFICE
CERTIFICATE OF CORRECTION

| | |
|---|---|
| PATENT NO. | : 8,163,274 B2 |
| APPLICATION NO. | : 11/895759 |
| DATED | : April 24, 2012 |
| INVENTOR(S) | : Rocco Burgo |

Page 1 of 1

It is certified that error appears in the above-identified patent and that said Letters Patent is hereby corrected as shown below:

On the Title Page, item (73) under the Assignee, add the Assignee Name as follows:

Inolex Investment Corporation

Signed and Sealed this
Eleventh Day of June, 2013

Teresa Stanek Rea
*Acting Director of the United States Patent and Trademark Office*